United States Patent [19]
Wada et al.

[11] Patent Number: 5,315,376
[45] Date of Patent: May 24, 1994

[54] METHOD AND APPARATUS FOR CORRECTING CONCENTRATION

[75] Inventors: Akio Wada, Hachioji; Mitsuo Watanabe, Aichi; Yoshikazu Yuki; Kazunori Ebisawa, both of Tokyo; Masashi Nishimoto, Kanagawa; Kazuhisa Hayashi, Aichi; Kiyoharu Kutsuna, Anjo; Takehito Mizutani, Oobu, all of Japan

[73] Assignees: JASCO Corporation, Tokyo; Nippondenso Co., Ltd., Aichi, both of Japan

[21] Appl. No.: 774,816

[22] Filed: Oct. 11, 1991

[30] Foreign Application Priority Data

Oct. 13, 1990 [JP] Japan ................................. 2-274039

[51] Int. Cl.$^5$ ............................................. G01N 21/01
[52] U.S. Cl. .................................... 356/432; 356/436; 356/437; 356/72; 356/43; 356/44; 356/45; 374/131
[58] Field of Search ................... 356/432, 128, 72, 43, 356/44, 45, 46, 47, 48, 436, 437; 374/131, 161

[56] References Cited

U.S. PATENT DOCUMENTS 3,840,305  10/1974  Sacarisen ........................ 356/432
4,883,354  10/1989  Sun et al. ........................ 356/72
5,003,175  4/1991  Fabinski et al. ..................... 250/345

Primary Examiner—Vincent P. McGraw
Assistant Examiner—LaCharles Keesee
Attorney, Agent, or Firm—Ronald R. Snider

[57] ABSTRACT

A concentration correcting apparatus comprising a correction coefficient calculating means and a correcting means is shown and described. The correction coefficient calculating means calculates a correction coefficient for correcting the concentration of the material when the actual density of the medium at the measurement of the material is calculated in terms of the density of the medium under the reference temperature and pressure, from the results of the temperature measuring means and the pressure measuring means. The correcting means corrects the results of the material measuring means to a concentration under the reference temperature and pressure on the basis of the correction coefficient. The measure value of the material in the medium under constant temperature and depressure is virtually calculated by correcting the measured value by using the correction coefficient while calculating the volume of the medium which is regarded as a parameter of a temperature and a pressure in terms of a volume under the constant temperature and pressure. It is therefore possible to calculate the concentration per unit weight under constant conditions even if the temperature and the pressure are varied at the time of measurement.

7 Claims, 2 Drawing Sheets

METHOD AND APPARATUS FOR CORRECTING CONCENTRATION

BACKGROUND OF THE INVENTION

1. Field of the Invention

The present invention relates to method and apparatus for correcting a concentration and, more particularly, to the improvement of a mechanism of correcting the measured concentration of a sample the volume of which varies with a pressure and a temperature.

2. Description of the Related Art

Optical means for measuring a predetermined ingredient in a liquid or a gas have found spreading use and, in particular, the absorbance measurement method is generally adopted for the measurement of concentration because it does not require complicated operation.

In the absorbance measurement method, the absorbance of a sample is measured, and the measured value is substituted into the preset equation of a calibration curve to obtain the concentration of the sample. This is based on the fact that the absorbance of the sample is dependent on the quantity (concentration) of a material being measured which is contained in a predetermined volume of the sample on the assumption that the volume of the sample does not change under any condition.

In the case of measuring an ingredient which is contained in a refrigerant such as flourocarbon and liquified carbon dioxide gas, however, the volume of such a medium varies with a pressure, temperature, etc., and the content of the material being measured per volume also varies with the change.

As a result, the concentration of the material per volume obtained is not proportional to the content per weight, which is required as a more substantial quantity, and it is impossible to obtain the accurate concentration per unit weight.

If a sample is measured under strictly constant pressure and temperature, this problem is solved. In order to realize this measurement, however, very strictly and complicated control of the measuring system is necessary. In addition, since the measuring conditions are different in apparatuses and measured absorbances, the objectivity of the measured data on the concentration of the material can not be expected.

SUMMARY OF THE INVENTION

Accordingly, it is an object of the present invention to eliminate the above-described problems in the related art and to provide method and apparatus for correcting a concentration measurement which are capable of obtaining the accurate concentration of the target ingredient contained in a medium the volume of which is apt to vary with a temperature and a pressure.

To achieve this aim, the present invention provides a concentration correcting apparatus comprising a correction coefficient calculator and a correcting means.

The correction coefficient calculator calculates a correction coefficient for correcting the concentration of a material being measured when the actual density of the medium at the measurement of the material is calculated in terms of the density of the medium under the reference and pressure, from the results of a temperature measuring means and a pressure measuring means.

The correcting means corrects the result of a material measuring means to a concentration under the reference temperature and pressure on the basis of the correction coefficient.

Since a concentration correcting means according to the present invention has the above-described means, it is possible to virtually calculate the concentration of a material in a medium under constant temperature and pressure by correcting the actual measured value by using the correction coefficient while calculating the volume of the medium which is regarded as a parameter of a temperature and a pressure in terms of a volume under the constant temperature and pressure.

It is therefore possible to calculate the concentration per unit weight under constant conditions even if the temperature and the pressure are varied at the time of measurement.

The correction coefficient calculating means preferably calculates correction coefficients $a_0$ and $a_1$ in the following equation:

$$C = a_0 + a_1 \cdot A$$

wherein C represents a concentration and A the measured density of a material, on the basis of the following equations:

$$a_0 = \alpha_0 \cdot \left(\frac{T}{P}\right) + \beta_0 \cdot \left(\frac{1}{P}\right) + \gamma_0 \cdot (T) + \delta_0$$

$$a_1 = \alpha_1 \cdot \left(\frac{T}{P}\right) + \beta_1 \cdot \left(\frac{1}{P}\right) + \gamma_1 \cdot (T) + \delta_1$$

wherein P represents a pressure, T a temperature and $\alpha_i, \beta_i, \gamma_i$ and $\delta_i$ constants.

It is preferable that a material measuring means, the temperature measuring means and the pressure measuring means are disposed in a refrigerant carrier pipe in a freezing refrigeration cycle and that the material measuring means measures the density of the oil which is contained in the refrigerant.

It is also preferable that the material measuring means, the temperature measuring means and the pressure measuring means are disposed in a refrigerant carrier pipe on the excurrent side of a gas-liquid separator in the freezing refrigeration cycle.

The above and other objects, features and advantages of the present invention will become clear from the following description of the preferred embodiment thereof, taken in conjunction with the accompanying drawings.

DESCRIPTION OF THE PREFERRED EMBODIMENT

An embodiment of the present invention will be explained hereinunder with reference to the accompanying drawings.

Figure 1:
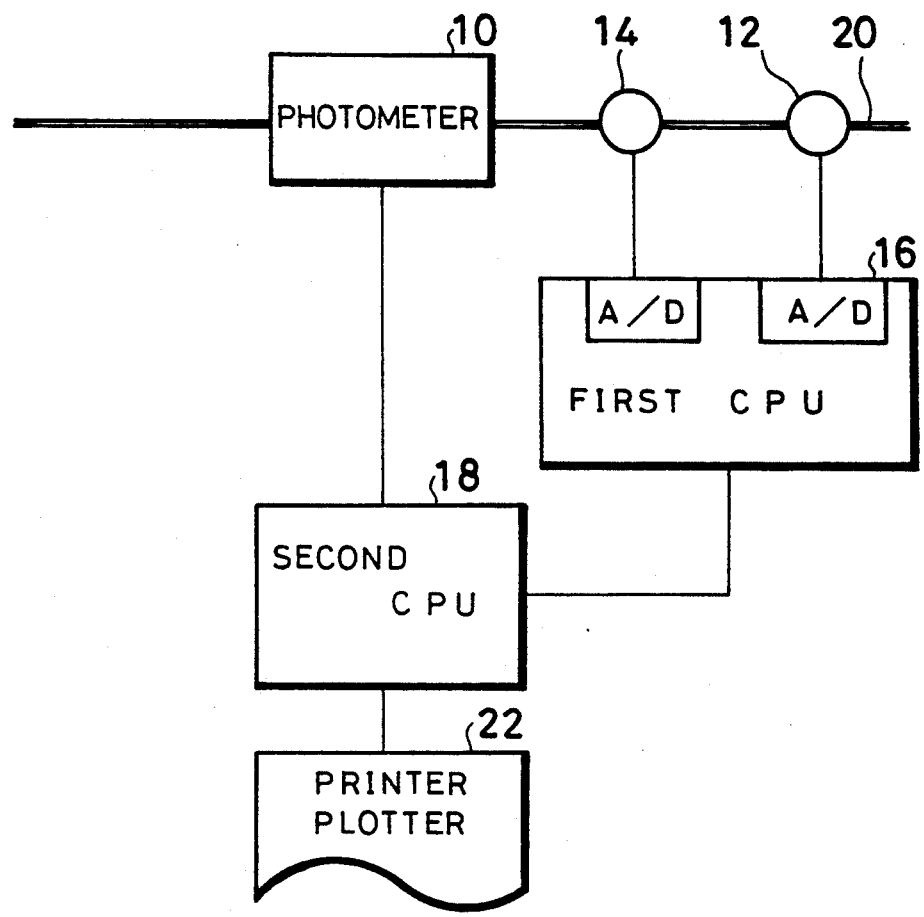
FIG. 1 is an explanatory view of the structure of an embodiment of a concentration measurement correcting apparatus according to the present invention.

FIG. 1 shows an embodiment of a concentration correcting apparatus according to the present invention which is applied to the measurement of an oil content in a refrigerant.

The concentration correcting apparatus shown in FIG. 1 is provided with a photometer 10 as a material measuring means, a temperature sensor 12 disposed in the vicinity of the photometer 10 as a temperature measuring means, a pressure sensor 14 disposed in the vicinity of the photometer 10 as a pressure measuring means, a first CPU 16 as a correction coefficient calculator and a second CPU 18 as a correcting means.

The photometer 10, the temperature sensor 12 and the pressure sensor 14 are connected to a refrigerant carrier pipe 20, and the photometer 10 measures the oil content per unit volume in the refrigerant by an ultraviolet absorbance. The temperature sensor 12 and the pressure sensor 14 measure the temperature and the pressure, respectively, of the refrigerant in the refrigerant carrier pipe 20. Since both sensors 12, 14 are disposed in the vicinity of the photometer 10 and the refrigerant carrier pipe 20 has a uniform diameter, the temperature and the pressure detected by the sensors 12, 14, respectively, agree with the temperature and the pressure of the refrigerant which is being measured by the photometer 10.

The first CPU 16 is provided with an A/D converter for converting the analog data output from the sensors 12, 14 into digital data, and calculates the correction coefficient for correcting the concentration of the oil when the actual density of the medium is calculated in terms of the density of the medium under the reference temperature and pressure.

The second CPU 18 corrects the data measured by the photometer 10 to a concentration under the reference temperature and pressure by using the correction coefficient.

The corrected result is displayed by a printer, plotter or the like 22 as a concentration (wt%).

Figure 2:
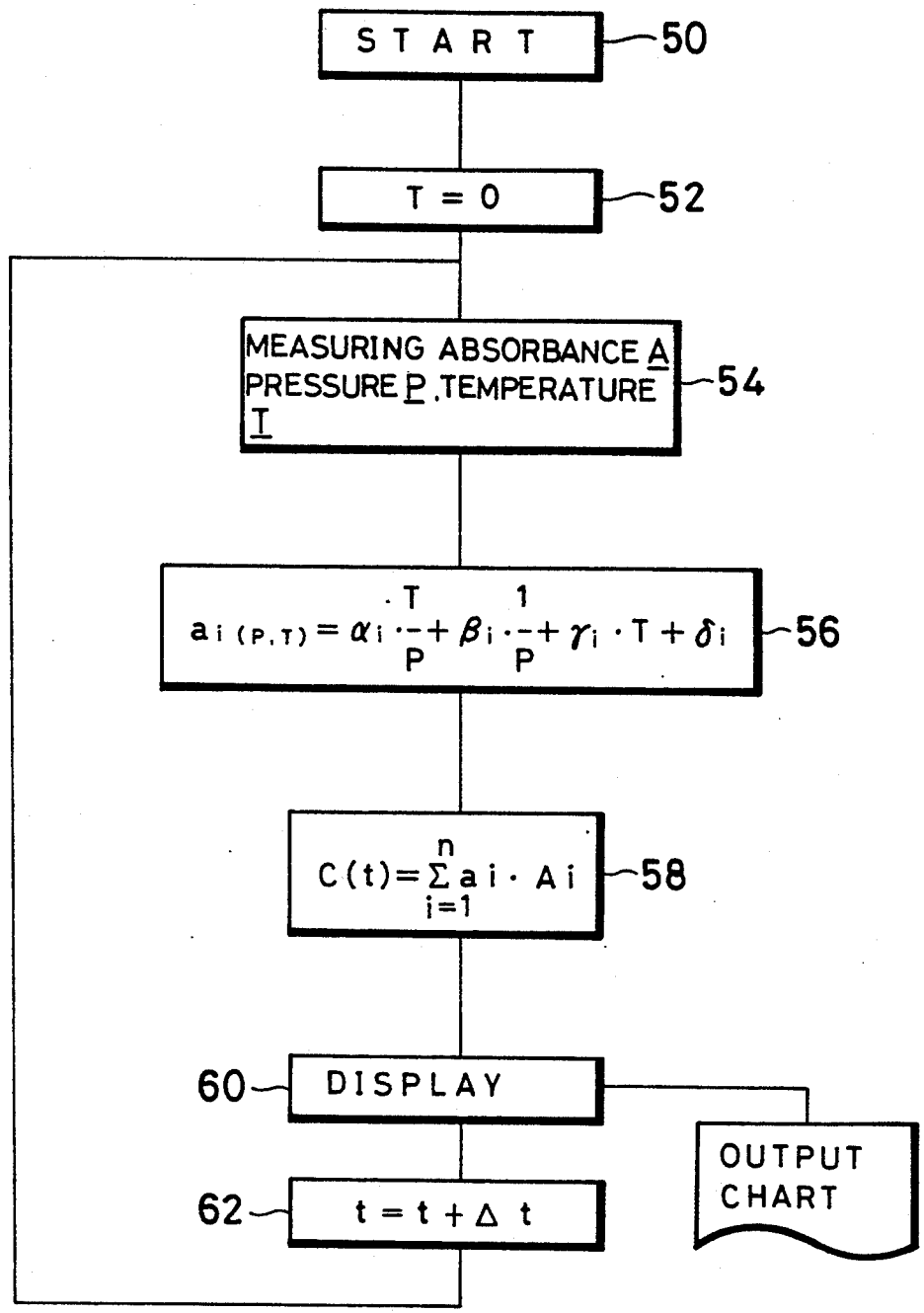
FIG. 2 is a flowchart of the operation of the apparatus shown in FIG. 1.

FIG. 2 is a flowchart of the operation of the concentration correcting apparatus shown in FIG. 1.

As shown in FIG. 2, when a measurement is started (step 50), a time function t is first reset to zero (step 52).

An absorbance A, a temperature T and a pressure P are then obtained from the photometer 10, the temperature sensor 12 and the pressure sensor 14, respectively (step 54).

A correction coefficient $a_{i(P, T)}$, which is dependent on the temperature T and the pressure P are next calculated by the first CPU 16 (step 56).

The second CPU 18 calculates the concentration C(t) at the time t on the basis of the correction coefficient $a_{i(P, T)}$ (step 58) and displays the result in the form of a chart or the like (step 60).

When this correction is finished, next measurement is started so as to measure the data after the lapse of a time $\Delta t$ (step 62).

In this way, according to the concentration correcting apparatus of this embodiment, it is possible to accurately calculate a trace ingredient in medium the volume of which greatly changes with a temperature and a pressure, for example, a refrigerant as a concentration per weight. In addition, it is also possible to serially measure the concentration (at a sampling interval of $\Delta t$) under constant conditions even if the temperature and the pressure vary moment by moment.

The correction coefficient used in the present invention will now be explained.

In this embodiment, on the basis of the fact that the concentration is proportional to the absorbance under constant temperature and pressure, the calibration curve represented by the following function system is adopted:

$$C = f_{(A)} \qquad (1)$$
$$= a_{0(P, T)} + a_{1(P, T)} \cdot A$$

wherein C represents a concentration, A an absorbance, P a pressure and T a temperature.

Since it is possible to treat the volume and the temperature dependence of a liquid (including a supercritical fluid) which is treated in the present invention in the same way as those of a gas, the following equation holds:

$$PV = K_1 \cdot T$$

wherein $K_1$ represents a constant.

Since $C \cdot V$ is constant in the same sample and the absorbance A is proportional to the concentration, $A \sim C$, hence, $A \cdot V$ is constant ($K_2$).

In order that the concentration obtained as the measured value is constant in the same sample irrespective of P and T, it is necessary that the following equation holds independently of P and T:

$$C = a_{0(P, T)} + a_{1(P, T)} \cdot A \qquad (2)$$
$$= a_{0(P, T)} + a_{1(P, T)} \cdot (P/T) \cdot K_1 \cdot K_2$$

That is, $a_{1(P, T)}$ must be proportional to T/P.

On the basis of the equation (2), the experimental formulas of $a_0$, $a_1$ are represented as follows:

$$a_0 = \alpha_0 \cdot \left(\frac{T}{P}\right) + \beta_0 \cdot \left(\frac{1}{P}\right) + \gamma_0 \cdot (T) + \delta_0 \qquad (3)$$

$$a_1 = \alpha_1 \cdot \left(\frac{T}{P}\right) + \beta_1 \cdot \left(\frac{1}{P}\right) + \gamma_1 \cdot (T) + \delta_1 \qquad (4)$$

$\alpha_j$, $\beta_j$, $\gamma_i$ and $\delta_i$ in the equations (3) and (4) are constants and they are determined, for example, by the least square of the values which are obtained by measuring a sample having a known concentration.

The above-described conclusions are also reached by another process.

Under certain pressure P and temperature T, the following equations hold:

$$C_{(P, T)} = a_0 + a_1 \cdot A_{(P, T)} \qquad (5)$$

$$C_{(P_0, T_0)} \cdot V_{(P_0, T_0)} = C_{(P, T)} \cdot V_{(P, T)} \qquad (6)$$

wherein $P_0$, $T_0$ represent reference pressure and temperature, respectively.

The equation (6) therefore becomes as follows:

$$C_{(P_0, T_0)} = C_{(P, T)} \cdot \left(\frac{P_0}{P}\right) \cdot \left(\frac{T}{T_0}\right) \qquad (7)$$

If the following equation is assumed to be the experimental formula:

$$C_0 = f(c) = \alpha \cdot \left(\frac{1}{P}\right) \cdot (T) + \beta \left(\frac{1}{P}\right) + \gamma \cdot (T) + \delta \qquad (8)$$

the same function system represented by the equations (1), (3) and (4) are finally obtained.

Although an impurity in a refrigerant is measured in this embodiment, the present invention is also applicable to the measurement of supercritical fluid, for example.

As described above, according to a concentration correcting apparatus of this embodiment, since a correction coefficient calculating means and a correcting means are provided, it is possible to obtain the accurate concentration per weight irrespective of a temperature and a pressure.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. A concentration measurement correcting apparatus comprising:
   a material measuring means for measuring the material which is an object of measurement in a medium as a density per unit volume;
   a temperature measuring means disposed in the vicinity of said measuring means so as to measure the temperature of said medium;
   a pressure measuring means disposed in the vicinity of said measuring means so as to measure the pressure of said medium;
   a correction coefficient calculating means for calculating correction coefficient $a_0$, $a_1$ in the following equation (1) for correcting the density measurement of said material when the actual density of said medium at the measurement of the material is calculated in terms of the density of said medium at a reference temperature and pressure from the results of said temperature measuring means and said pressure measuring means on the basis of the following equations (2) and (3):

$$C = a_0 + a_1 \cdot A \qquad (1)$$

wherein C represents a concentration, A the measured density of said material, $$a_0 = \alpha_0 \cdot \left(\frac{T}{P}\right) + \beta_0 \cdot \left(\frac{1}{P}\right) + \gamma_0 \cdot (T) + \delta_0 \qquad (2)$$

$$a_1 = \alpha_1 \cdot \left(\frac{T}{P}\right) + \beta_1 \cdot \left(\frac{1}{P}\right) + \gamma_1 \cdot (T) + \delta_1 \qquad (3)$$

wherein P represents a measured pressure, T a measured temperature and $\alpha_i$, $\beta_i$, $\gamma_i$ and $\delta_i$ constants and correcting means for correcting the result of said material measuring means to a density measurement at said reference temperature and pressure by said correction coefficient.

2. The apparatus in accordance with claim 1 wherein the material measured has a volume which varies with pressure and temperature.

3. An apparatus according to claim 2,
   wherein said material measuring means, said temperature measuring means and said pressure measuring means are disposed in a refrigerant carrier pipe in a refrigeration cycle; and
   said material measuring means measures the density of the oil contained in said refrigerant pipe.

4. An apparatus according to claim 2
   wherein said material measuring means, said temperature measuring means and said pressure measuring means are disposed in a refrigerant carrier pipe on the excurrent side of a gas-liquid separator in the freezing cycle; and
   said material measuring means measures the density of the oil contained in said refrigerant pipe.

5. A method of correcting a concentration measurement comprising the steps of:
   measuring the material which is an object of measurement in a medium as a density per unit volume;
   measuring the temperature of said medium;
   measuring the pressure of said medium;
   calculating a correction coefficient for correcting the density measurement of said material when the actual density of said medium at the measurement of material is calculated in terms of the density of said medium of a reference temperature and pressure from the results of said temperature measuring means and said pressure measuring means; and
   correcting the result of said material measuring means to a density at said reference temperature and pressure by said correction coefficient.

6. A method of correcting a concentration measurement comprising the steps of:
   measuring the material which is an object of measurement in a medium as a density per unit volume;
   measuring the temperature of said medium;
   measuring the pressure of said medium;
   calculating correction coefficients $a_0$, $a_1$ in the following equation (1) for correcting the density measurement of said material when the actual density of said medium at the measurement of the material is calculated in terms of density of said medium at a reference temperature and pressure from the results of said temperature measuring means and said pressure measuring means on the basis of the following equation (2) and (3):

$$C = a_0 + a_1 \cdot A \qquad (1)$$

wherein C represents a concentration, A the measured density of said material, $$a_0 = \alpha_0 \cdot \left(\frac{T}{P}\right) + \beta_0 \cdot \left(\frac{1}{P}\right) + \gamma_0 \cdot (T) + \delta_0 \qquad (2)$$

$$a_1 = \alpha_1 \cdot \left(\frac{T}{P}\right) + \beta_1 \cdot \left(\frac{1}{P}\right) + \gamma_1 \cdot (T) + \delta_1 \qquad (3)$$

wherein P represents a measured pressure, T a measured temperature and $\alpha_i$, $\beta_i$, $\gamma_i$ and $\delta_i$ constants; and correcting the result of said material measuring means to a density at said reference temperature and pressure by said correction coefficient.

7. The method in accordance with claim 6 wherein the material measured has a volume which varies with pressure and temperature.

* * * * *